United States Patent [19]
Cropper

[11] Patent Number: 5,735,807
[45] Date of Patent: Apr. 7, 1998

[54] SOFT TISSUE COMPRESSION SUPPORT

[76] Inventor: Dean E. Cropper, 240 E. Hershey St., Ashland, Oreg. 97520

[21] Appl. No.: 396,468

[22] Filed: Mar. 2, 1995

[51] Int. Cl.$^6$ .................................................. A61F 5/00
[52] U.S. Cl. .............................. 602/63; 602/26; 602/62
[58] Field of Search ........................ 602/20, 26, 27, 602/75, 77, 63, 110, 60, 62; 128/881, 882

[56] References Cited

U.S. PATENT DOCUMENTS

| | | | |
|---|---|---|---|
| 4,084,584 | 4/1978 | Detty | 602/63 |
| 4,765,318 | 8/1988 | Tranberg et al. | 602/26 |
| 5,085,210 | 2/1992 | Smith, III | 602/26 |
| 5,221,252 | 6/1993 | Caprio, Jr. et al. | 602/26 X |
| 5,267,951 | 12/1993 | Ishii | 612/26 |
| 5,382,223 | 1/1995 | Springs | 602/26 X |

*Primary Examiner*—Richard J. Apley
*Assistant Examiner*—Kim M. Lee
*Attorney, Agent, or Firm*—Robert L. Harrington

[57] ABSTRACT

A soft tissue support particularly suited for the treatment of muscle injuries. The support is constructed of a thin highly elastic material having a four-way stretch capability. The material has outer layers of a nylon like material bonded to a thin inner layer of polyurethane material. The nylon like material provides for comfort and adds to the strength of the material. The inner layer is highly resilient and retains its elasticity. The support being of highly elastic, thin material readily conforms to the body portion to which it is fitted and applies a uniform compressive force to the body portion as the body portion changes in dimension due to muscle flexing. The support retains therapeutic body heat while still allowing breathability (air flow), due to its porosity to reduce perspiration build up.

6 Claims, 1 Drawing Sheet

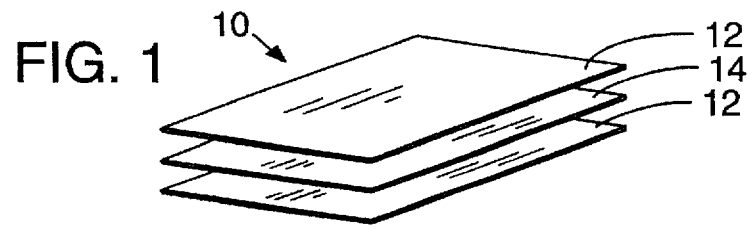
FIG. 1
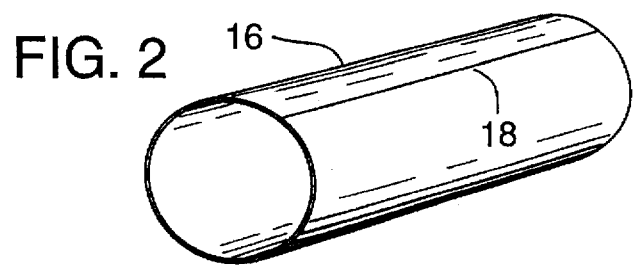
FIG. 2
FIG. 3     FIG. 4 Prior art
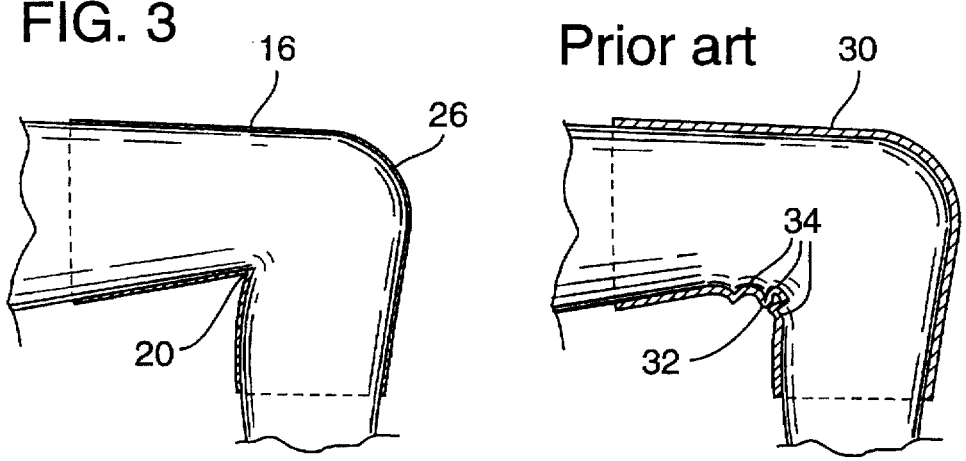
FIG. 5
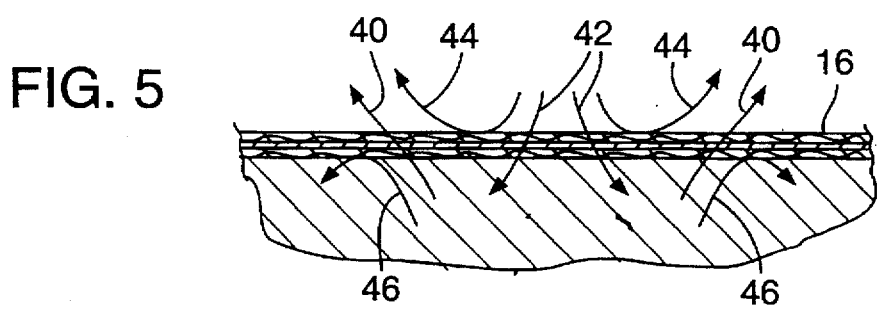
FIG. 6 Prior art
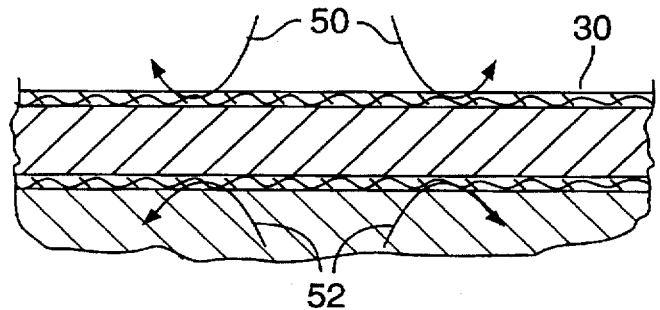

5,735,807

SOFT TISSUE COMPRESSION SUPPORT

FIELD OF THE INVENTION

This invention relates to compression sleeves or wrappings to injured areas often associated with sports, occupational and industrial injuries.

BACKGROUND OF THE INVENTION

There are various types of injuries which result in tissue injuries. Common injuries include, over use causing tendinitis, contact injuries which can lead to torn cartilage or contusions, strains, sprains and others. Such injuries often occur when a person is participating in a rigorous activity either through a sporting activity or through their occupation.

Typically all such injuries heal over a period of time, but depending on the injury it can be lengthy and medical attention is needed. Early healing time and quick return to full function is always the goal.

However, due to the nature of many injuries this goal is not achieved without rehabilitation, modification of the activity or in many cases surgical intervention. In all of the above cases, pain is a continued factor wince the affected muscles and joints are in continued use.

It has been learned that the pain associated from such injuries could be significantly reduced by using a compressional wrap over the injured area. A tight and unyielding wrap restricts movement as well as blood circulation and is not desirable. It is determined that an elastic wrap would alleviate the pain with less restriction of movement. Initially, the wrap was an elongated narrow band of elastic material that was wrapped around the injured area multiple times in a layered arrangement. It was difficult to achieve the desired compression on the injury. If the wrap was too loose, it provided little if any benefit. If the wrap was too tight, it would restrict the blood circulation and often add to the discomfort the injured person was already experiencing. Even if the wrap was put on properly, the wraps would migrate and loosen rendering the wrap ineffective.

Neoprene sleeves were developed that slide over the injured area of a person. The sleeve maintains a yieldable resistance that is less bulky and less likely to loosen or slip. Such Neoprene sleeves have been the standard for treating tissue injuries for years. Neoprene nevertheless brings its own problems to the injured area. Whereas the compression from the Neoprene helps to alleviate the pain from the injury, the sleeve resists bending, prevents the skin from breathing making the treated area hot and sweaty, it causes rashes and blistering to 5% of the people who use it. Because it is so bulky, a number of Neoprene products cannot be worn under clothes. Due to the bulk there is a bunching and gathering problem in the joints. The gathered material becomes non-elastic and in effect loses its compression. Neoprene loses its ability to compress and the length of time depends on the quality of the material.

BRIEF DESCRIPTION OF THE PRESENT INVENTION

One of the misconceptions about a compressive sleeve is a belief that the sleeve must be semi-rigid (and thus somewhat bulky) to provide the optimal joint support. Thus, the semi-rigid support will add to the structural integrity and support of the joint. It is the applicant's belief (and tests have largely substantiated those beliefs) that the relief of pain results from adequate soft tissue compression which facilitates soft tissue alignment in the joint structure which allows anatomical or normal alignment to the malaligned joint which occurred as a result of injury. Due to the fact that an injured joint typically becomes unstable due to the swelling and lack of proprioceptive sensation, a compressive support that acts as a second layer of skin offers the neurological proprioceptive feedback and the additional soft tissue support that is necessary to the joint of the affected area to function at a normal or higher performance level.

Regardless of what is perceived to be the anatomical effect of the support, applicant has provided all the pain reducing benefits of a thick bulky Neoprene sleeve or wrap using a material that is a fraction of the thickness. Applicants supports are far more flexible, tests have shown the material to be 3 to 4 times stronger than Neoprene, they do not gather or pinch, they have greater porosity and thermal release value that significantly reduces the incidence of contact dermatitis which requires that the product use be discontinued or some type of additional interface be put between the sleeve and the skin. To date there has not been one reported case of skin sensitivity or dermatitis with the applicant's supports.

Numerous variations of the supports are available as will be discussed in the detailed description that follows. Basically, the material of the support sleeve of the present invention is a laminate including a polyurethane membrane and a stretchable fabric preferably on both sides of the membrane. Due to the varied athletic levels of those who wear the product, the support can encounter significant abuse so the strength of the material is vital for its continued use and longevity. The principal strength that is derived from Neoprene is from the thin nylon laminate bondable to the Neoprene rubber. As the Neoprene breaks down either through time or through use, the products easily rip and can lose as much as 30% of its compression ability. The applicant's product on the other hand is fabricated in an entirely different type of laminating process and totally different materials. The applicant utilizes a 1 mil(0.001 inch) thick polyurethane membrane and bonds them to the stretchable fabric at each side through a heat, glue and pressure process. The polyurethane membrane with the laminated fabric provides an increase of strength by 300%–500%. This increased strength along with the greater dynamic ability of the material to function anatomically and dynamically provides a more consistent level of compression throughout any anatomical range of motion. Because of this built in strength of the fabric from the materials and the laminating process, the support does not lose a significant amount of elasticity over a long period of time. The material is available under the trademark name of BIO SKIN which is produced at Fabrite Laminators.

Another factor that comes into play is that neoprene upon becoming wet due to perspiration begins to migrate out of position. This is easily shown by viewing any sport where the neoprene support can be seen. There is always bunching of the neoprene around the knee. Also, in many cases it has slid down the knee out of position, thus rendering the support ineffective.

The Bio Skin fabric of the present invention achieves just the opposite effect. Since these supports are almost always used in athletic activities, the user will perspire in them. The physical properties of the Bio Skin material change when they are wet or damp. It has been shown that the Bio Skin's coefficient of friction increases as the fabric and skin get wet. This plays a significant role in the function of the product. This feature "locks" the product in place to insure proper positioning of the support is maintained as long as the support is worn.

The thick bulky nature of neoprene has physiological problems. During flexion of the knee specifically, but the problem happens in other joints, neoprene bunches in the area of the most sensitive areas of the body because the popliteal nerve and the major blood vessels that supply blood below the knee pass through this area. When the knee is flexed with a neoprene support on, like a basketball player would do when sitting on the bench during a game, there is enough pressure from the bulk of the neoprene behind the knee joint to reduce the blood flow and apply pressure to the nerves making it very uncomfortable and also diminishing athletic performance of the participant.

Due to the thin nature of Bio Skin, coupled with the dynamic change of the fabric when it gets wet through perspiration to act as a second layer of skin, there is no bunching and binding behind the knee or other joints to cause the stated problems.

The advantages discussed will be more fully appreciated by reference to the following detailed description and drawings.

BRIEF DESCRIPTION OF THE DRAWINGS

FIG. 1 is a view illustrating the layers of the material utilized in the soft tissue support of the present invention;

FIG. 2 is a view of a soft tissue support of the present invention;

FIG. 3 is a view of a soft tissue support of the present invention fitted to a knee of an individual;

FIG. 4 is a view of a support of the prior art;

FIG. 5 is a view illustrating the porosity of the soft tissue support of the present invention; and, FIG. 6 is a view illustrating the porosity of a support of the prior art.

DESCRIPTION OF THE PREFERRED EMBODIMENT

Refer now to FIG. 1 of the drawings which illustrates a manner of producing a material 10 utilized in the soft tissue supports of the present invention. The material 10 is preferably of three layers that are laminated and/or bonded together in a conventional manner to produce a thin material that has what is referred to as four way stretch capability. The material 10 has two outer layers of fabric 12, such as nylon, that has four way stretch capability. The middle or center layer 14 (membrane) is of polyurethane material that also has a four way stretch capability. The outer layers 12 and the center layer 14 are laminated (bonded) together by known techniques to provide a material 10 that has characteristics beneficial for soft tissue supports of the present invention. The material 10, produced by laminating the layers 12, 14 together is thin, it is very pliable, it has great strength, it has four way stretch capability, it has high elasticity retention and it has a porosity factor on the order of 35%.

The material 10 is readily formed (fabricated) into a desired configuration by conventional sewing techniques since it is thin and very pliable. The material 10 for most applications is on the order of 0.025 to 0.045 inch thick, however the material 10 may be produced in other thicknesses to suit the application. A support 16 (sleeve), such as for an elbow, knee, wrist and the like, as illustrated in FIG. 2 is produced by simply cutting the material to a desired pattern and sewing two edges together at seam 18 to produce a desired cylindrical like shape of a size to closely fit the body portion for which it is intended to be applied.

The thread or cord utilized to join (sew) the two edges of the material 10 at seam 18 is preferably of an elastic material and the stitching is of a known type that provides the seam 18 with substantially the same stretch capability as the material 10. It will be appreciated that the two edges may be joined together by other known methods such as by adhesively bonding the two edges together or by laser or ultrasonic welding. The pliability in conjunction with the four way stretch capability of the material 10 (and the seam 18) permits the material to readily conform to the contours of the body parts such as an elbow area, wrist area and so forth.

FIG. 3 illustrates a soft tissue support 16 of the present invention fitted to an knee area of an individual. The support 16 which is constructed from the material 10 readily conforms to the varying contour of the knee area due to its elastic properties and the pliability of the thin material. The four way stretch capability and the elasticity of the support will apply a uniform retentive force and a mild compressive force to the area of the knee that the support surrounds. The support 16 will resistively conform to the changes inherent to the flexing of the knee joint. That is, as the knee joint is flexed, the muscles associated with the knee area will flex and change in their diametral size and the support 16 will elastically conform to the changes but at the same time will apply a consistent resistive force to the area which the support surrounds. Slow expansion is accomplished with little resistive force whereas rapid expansion is accomplished with strong resistive force. Thus, the sleeve is comfortable for slow movements and produces binding support to resist rapid expansion due to stressful movements of the body part.

An added benefit inherent with the thin material 10 of the support 16 is the minimal folding or bunching of the support 16 at the joint area 20 of the knee as the individual bends the knee as seen in FIG. 3. Compare this with the bunching or folding of the thicker bulkier support 30 of the prior art as illustrated in FIG. 4. The bunching or folding of the support 30 at the joint area 32 is much more pronounced and has large folds 34 that tend to pinch or produce excessive compression in the joint area 32 that could result in added discomfort to the individual and in some cases even restricting blood flow. This may occur for example when the joint is in a prolonged fixed position like sitting on the bench during a basketball game.

An additional benefit of the thin material 10 utilized in the supports of the present invention is its porosity factor, which is on the order of about 35 per cent. The porosity of the material 10 allows air flow through the material yet has a heat retention property. The material 10 of the support 16 as depicted in FIG. 5 allows some air flow (breathing) through the material 10 as indicated by the arrows 40, 42. The heat retention quality is indicated by arrows 44 which depicts some of the external air (heat or cold) from entering through the material and by arrows 46 which depicts some of the internal air (body heat) from exiting through the material 10. The unique properties of the material 10 help retain therapeutic heat while still allowing breathability (air flow) to reduce perspiration build up.

FIG. 6 depicts the thick bulky non-permeable support 30 of the prior art and as shown air flow through the support is virtually non existent as indicated by the arrows 50, 52. The support 30 of the prior art, since air will not flow through it, does not permit the escapement of heat (body heat) and excessive perspiration build up is likely to occur.

The material 10 readily accommodates ancillary appliances such as braces, auxiliary support straps, patella stabilizers and the like. The support described and illustrated is for a knee however the material 10 is suited for other applications as mentioned previously such as supports for ankle, wrist, thigh, shin and others. The material 10, being thin, is also well suited for a torso wrap, such as for the lower back. The invention can take many different forms including strap and pad attachments and the like.

Whereas polyurethane such as used for layer 14 and fabric 12 (e.g., nylon) are known materials, they have not been combined to produce material 10 or utilized as a body support as illustrated in FIG. 3. The material 10 is a modification of certain materials produced by Fabrite Laminators. The material 10 is customized to produce the desired voracity and stretch characteristics. A specific example of the material 10 which has been used for producing the illustrated knee wrap is (a) Lycra material available from Liberty Fabrics, Style No. 7043 and (b) Polyurethane membrane, one mil (0.001 inch) thick produced by Fabrite Laminators, Style No. 6100. The materials (a) and (b) were laminated using a process including heat, pressure and glue. The process as optimized produces a laminate which requires at least 25 PSI to detach or delaminate the material.

Those skilled in the art will recognize that modifications and variations may be made without departing from the true spirit and scope of the invention. The invention is therefore not to be limited to the embodiments described and illustrated but is to be determined from the appended claims.

I claim:

1. A compression support for a body portion of a person having a tissue injury in said body portion comprising:

a laminate material no greater than about 0.025 to 0.045 inch thickness and comprised of a polyurethane membrane no greater than about 0.001 inch thickness and a stretchable material covering said membrane, said material formed into a sleeve for enveloping said body portion, maid sleeve in a stretched state having the property of low active compressibility force and strong passive resistance to expansion with the resistance to expansion substantially greater than the compressibility force.

2. A compression support as defined in claim 1 wherein said laminate material has a porosity factor of about 35 percent.

3. A compression support as defined in claim 2 wherein the material as the stretchable material is a sheet material formed by bonding the stretchable synthetic material as the stretchable material to polyurethane membrane, the sheet material formed into a tubular form with side edges secured together.

4. A compression support as defined in claim 3 wherein various straps and pads are sewn to the sheet material for enhanced support as determined desirable for the injured body portion.

5. A compression support as defined in claim 3 wherein the weave of stretchable fabric creates a co-efficient of friction that resists slipping on the person's body portion.

6. A compression support as defined in claim 2 wherein said porosity factor in combination with the material applied against the body portion avoids perspiration build up under the support to reduce irritability to the underlying body portion.

* * * * *

UNITED STATES PATENT AND TRADEMARK OFFICE
CERTIFICATE OF CORRECTION

PATENT NO. : 5,735,807
DATED : 4/7/98
INVENTOR(S) : Cropper

It is certified that error appears in the above-indentified patent and that said Letters Patent is hereby corrected as shown below:

Col. 6, line 4, change "maid" to --said--.

Signed and Sealed this

Twenty-third Day of June, 1998

Attest:

BRUCE LEHMAN

*Attesting Officer*      *Commissioner of Patents and Trademarks*